United States Patent [19]
O'Connor

[11] Patent Number: 6,029,659
[45] Date of Patent: *Feb. 29, 2000

[54] INHALATION DEVICE WITH COUNTER

[75] Inventor: James A. O'Connor, Ulster Park, N.Y.

[73] Assignee: Solar Shield Corporation, Ulster Park, N.Y.

[*] Notice: This patent is subject to a terminal disclaimer.

[21] Appl. No.: 08/423,228

[22] Filed: Apr. 17, 1995

[51] Int. Cl.[7] .......................... A61M 15/00; A61M 16/10
[52] U.S. Cl. .............................. 128/203.12; 128/200.23; 128/203.15
[58] Field of Search .................... 128/200.14, 200.23, 128/200.24, 200.22, 203.12, 205.23, 203.15

[56] References Cited

U.S. PATENT DOCUMENTS

| | | | |
|---|---|---|---|
| 4,296,756 | 10/1981 | Dunning et al. | 128/716 |
| 5,020,527 | 6/1991 | Dessertine | 128/200.23 |
| 5,284,133 | 2/1994 | Burns et al. | 128/200.23 |
| 5,328,597 | 7/1994 | Boldt, Jr., et al. | 222/38 |
| 5,333,106 | 7/1994 | Lanpher et al. | 364/413.01 |
| 5,348,008 | 9/1994 | Bornn et al. | 128/642 |
| 5,363,842 | 11/1994 | Mishelevich et al. | 128/200.14 |
| 5,392,768 | 2/1995 | Joharsson et al. | 128/200.14 |
| 5,404,871 | 4/1995 | Goodman et al. | 128/200.14 |
| 5,411,173 | 5/1995 | Weinstein | 222/38 |
| 5,544,647 | 8/1996 | Jewett et al. | 128/200.23 |
| 5,564,414 | 10/1996 | Walker et al. | 128/200.23 |

Primary Examiner—John G. Weiss
Assistant Examiner—Joseph F Weiss Jr.

[57] ABSTRACT

An inhalation device in the nature of a metered dose inhaler with a counter is disclosed. The device is designed to work with existing respiratory drugs. The device is comprised of a L-shaped medication dispenser in which a counter is attached. A downward force applied to the top portion of the canister protruding from the top of the L-shaped medication dispenser releases a single dose of the aerosol medication and increments the counter. The device contains a visual display of the current count and thus an indication of the metered doses remaining in the aerosol canister. The counter can be electronic, mechanical or electro-mechanical in nature. Counting devices for other shaped dispensers such as cylindrical dispensers are also described. Other options such as a warning alarm, automatic power conservation shutdown of the display, and full computer monitoring functions are also disclosed.

9 Claims, 10 Drawing Sheets

INHALATION DEVICE WITH COUNTER

BACKGROUND OF THE INVENTION

The occurrences of asthma continue to rise each year. One in five Americans, roughly 50 million people, suffer from an allergic disease. Asthma and allergies are the most common chronic diseases in this country. There are also many individuals that suffer from chronic bronchitis or emphysema. Many of the individuals afflicted with these ailments use a metered dose inhaler (MDI). The MDI is by far the most common and effective treatment for most respiratory problems.

The most common MDI device currently in use is comprised of a L-shaped dispenser and an aerosol canister. The aerosol canister contains medication and is capable of delivering a finite number of metered doses of pressurized medication. The aerosol canister is inserted into the L-shaped dispenser with the hollow stem of the canister pointing downward.

The patient self administers the medication. The open end at the bottom of the L-shaped dispenser is placed near the patient's mouth before the medication is released. A single push on the canister releases a single dose of the medication in the form of an inhaled aerosol. The downward pressure is placed on the top of the aerosol canister which protrudes from the opening in the L-shaped dispenser in which the canister was inserted. The downward pressure forces the hollow tube of the canister back into the canister which releases a single dose of the medication.

A significant deficiency of MDI's is the inability of the patient to precisely determine how many metered doses of medication remain in the aerosol canister. A patient without medication that has a serious respiratory problem can find themselves in a life threatening situation.

The consequences of an untreated asthma attack can be deadly. A serious asthma attack can result in a combination of swelling of the lungs and muscular constriction of the airways with little or no air movement beyond the obstruction. The lungs become over inflated since the patient cannot exhale air within their lungs. The air remains trapped in the lungs and the routine exchange of oxygen with carbon dioxide cannot occur. Carbon dioxide builds in the bloodstream. The situation is life threatening.

Each year in the United States an estimated four thousand deaths occur due to asthma alone. A key factor putting the patient at risk is failure or inability to comply with the medication program suggested by the doctor.

There is currently no simple procedure to determine the number of metered doses of medication remaining in the aerosol canister. The recommended procedure to check for an empty or nearly empty aerosol medicine canister is to remove the canister from the L-shaped delivery device to see if the canister floats or sinks in a glass of water. This method may be difficult to execute when the patient is away from home. Most patients simply shake the aerosol canister from the L-shaped dispenser in an attempt to determine if it is empty or nearly empty. This method is highly inaccurate and can result in the patient believing that they are continuing to receive full doses of medication well after the canister has passed the point of effective delivery. This is true because when depressed, the pressurized canister will continue to expel some amount of medication well after the point where it delivers the full metered dose. On the other hand, the patient might also believe that there is a good deal of medication remaining in the canister and fail to take additional medication along when leaving home.

The situation is further complicated when less instantaneous, longer acting, preventative medications are considered. A patient using a quick acting asthmatic medication, such as bronchodialator like albuterol (Proventil or Ventolin) can normally determine quite quickly if they are getting a proper dose of medication, since the patient expects to get relief from the asthma attack almost immediately. Slower acting drugs, such as inhaled steroids or cromolyn sodium (Intal) target the inflammation in the lungs, not the constricted muscles of bronchial tubes. Most preventative medications require several doses over a period of days to be fully effective. It is virtually impossible for a patient to determine if they are receiving the proper amount of a preventative medication at the time of inhalation by the immediate effect on their body.

Electronic, mechanical, and electro-mechanical counting devices have found their way into many aspects of modern society. Mechanical counting devices are comprised of a series of moving parts that can calculate information. These devices can be as simple as a mechanical hand counter used by an usher at a gate to track the number of patrons entering an event. Mechanical counting devices are often found with analog mechanical displays. These displays can be use to indicate information such as a the current time or a value. One form of an analog mechanical display is one or more moving hands that points to a value that is listed on a background display. It is also common to see analog mechanical displays in the form of synchronized rotating wheels with decimal numbers displayed on the external rim of each wheel in which only one decimal number per wheel is visible at any one time. Internal gear or other moving parts are used to synchronize and increment the hand or wheels of the display.

It is common to find a mechanical reset button associated with a mechanical counter that when pushed will align the internal mechanical parts to point to a predetermined starting value to reset the counter. It is also common on a wrist watch to find one or more knobs that can be turned to rapidly change the display to some desired value.

The relatively large number of moving parts typically make mechanical counting and computing devices more difficult to manufacture; especially when a miniature device is required. One clear advantage of mechanical calculators is the ability to construct them without the need of a power supply, such as a battery.

VLSI (Very Large Scale Integration) and low power CMOS (Complementary Metal Oxide Semiconductors) have made it possible to create extremely small low power electronic and electro-mechanical computing devices with a wide range of functions and capabilities. Electronic and electro-mechanical devices can take the form of a wristwatch or a camera. Wristwatches can be found that are totally electronic with digital readout such as LED (Light Emitting Diode) displays or LCD (Liquid Crystal Displays). Wristwatches can also be found that are a combination of electronic counting circuits and mechanical analog displays in the form of an hour and minute hand. One clear disadvantage of the electronic or partially electronic watch is the need to periodically replace the battery. Fortunately, battery replacement may not be necessary for years which makes it an acceptable burden and perhaps easier than winding a wristwatch every few days.

Small, more complex electronic devices can also be found today. They may take the form of a computer with not just counting circuits but a complex set of programmable instructions and a time-of-day clock. When connected to peripheral input/output devices, such devices can provide a wealth of functions and handle very complex tasks. One place we see this is in small compact cameras and video recording equipment.

Despite a limited life, due to the finite power provided by a battery, electronic and electro-mechanical counting devices are normally much easier and less complicated to manufacture than mechanical devices. This is certainly true when one compares function to the number of moving parts and size. Electronic and electro-mechanical devices can normally be produced in very small compact packages. Again, this is primarily due to the advances in VLSI circuit design technic and that they can be produced with few, if any moving parts.

An electronic device offers the ability to add additional functions at low cost. Unlike a mechanical counter, a power supply normally in the form of a battery is required. The use of low power CMOS, a LCD display, and a small cylindrical battery can produce a device that can last a very long time without the need to replace the battery. This period of time can be extended even further if a timed auto-shutdown circuit is employed, which allows the display and any non-critical circuits, other than the latches holding the count to be powered off, in order to prolong the life of the battery. Inexpensive, non-replaceable batteries can be found in some applications, especially for disposable devices. This can further reduce cost and complexity in manufacturing.

The counting device can be made as simple or as elaborate as desired. Naturally, there is a tradeoff between function and cost. Electronic computers and counters have been equipped with a circuit that drives a small plastic speaker. We find such speakers on wristwatches where they produce an audible alarm. We also find automatic power off circuits that cut power to the display after some timed interval to conserve power.

SUMMARY OF THE INVENTION

The present invention relates to improvements in medicated inhalers.

It is an objective of the present invention to provide patients with a means to more precisely determine the amount of medication in an inhalation device. This will reduce the likelihood of a patient inadvertently being without medication or attempting to administer medication from an inhaler incapable of delivering a full dose.

One form of the invention is an inhalation device in the nature of a metered dose inhaler with a counter. It is an objective of the invention to work with existing respiratory drugs. It is yet another objective of the invention to allow the device to be constructed from a modified version of the standard L-shaped medication dispenser with an electronic, mechanical, or electro-mechanical counter attached. Another objective of the invention is to allow the counter to be automatically incremented when the downward force applied to the top portion of the canister protruding from the top of the L-shaped dispenser releases a single dose of the aerosol medication. Another objective of the invention is to provide a visual display of the current count and thus an indication of the number of metered doses of medication remaining in the aerosol canister.

One form of the invention is constructed by providing a hole in the L-shaped medication dispenser in which a counter is attached. A counter is inserted into this hole and fastened to the L-shaped medication dispenser. The counter being either electronic, mechanical, or electro-mechanical would have a push button on the top that aligns with the direction the aerosol canister moves when depressed. When the canister is depressed to release the medication the counter is automatically incremented. When the canister is depressed to release the medication, the button on the counter is also depressed by the movement of the canister and thus the counter is automatically incremented displaying a count of metered doses administered from the aerosol canister.

I only briefly describe the operation of mechanical, electronic, and electro-mechanical counting devices since they are common place in the art. Much of this technology has been applied to the portable electronic's industry where small low cost mechanical, electronic, and electro-mechanical counting devices are in use to count, compute, track time, and track dates.

One form of the invention is composed of electronic or a combination of electronic and mechanical parts. Another objective of the invention is to make the device compact. Another objective is to make the device relatively easy to manufacture. Despite a limited life, due to the finite power provided by a battery, electronic and electro-mechanical counting devices are normally much easier and less complicated to manufacture. They can also normally be produced in a much more compact package. This form of the invention is primarily due to the advances in VLSI circuit design technic, since it can be produced with few if any moving parts.

VLSI circuits make it possible to add additional functions to electronic counters at a low cost. Unlike mechanical counters, electronic counters require a power supply, normally in the form of a battery. The combination of low power CMOS, a LCD display, and a small cylindrical battery make it possible to produce a compact, device that will operate a very long time without the need to replace the battery. This period of time can be extended even further if a timed auto-shutdown circuit is employed, which allows the display and other nonessential portions of the electronic circuits, other than the latches holding the count, to be powered-off in order to prolong the life of the battery. Some applications also use non replaceable batteries for disposable devices in order to further reduce cost and complexity in manufacturing.

Another objective of the invention is to produce a design where special features and functions can be added easily. The VLSI circuits of this computing device can be made as simple or elaborate as desired. This naturally is a tradeoff of function versus cost. Again, VLSI offers the opportunity to add additional circuits with little increases in cost.

Another objective of the invention is to equip the device with a circuit to drive a small plastic speaker that could produce an audible alarm. The alarm might sound when the medication is depleted or nearly depleted. The alarm could also be used to warn the patient that it is time or past time to take their medication.

Another objective is to provide an external interface so the device can be connected to other devices to communicate and exchange information. Another objective would be to have the speaker drive the audio interface to a modem to establish a communication interface with a remote computer. Information related to the patient could be exchanged and the calculating device could be reset or loaded with new information related to the patient. Another objective is to provide a physical electrical external interface. This interface might be a small telephone jack that would allow the device to again communicate with a remote computer through a series of electrical signals. There are countless standard protocols and interfaces that could be used for this purpose, such as FSK (Frequency Shift Keying).

Another objective is to provide an optional external DC jack as a charger for the battery.

Other features might include an automatic power-off circuit that would cut power to the display after some timed interval to conserve power. A separate button could be provided to re-energize the display without incrementing the counter or the display could be re-energized for some period of time after a dose of medication is administered. A single multiple contact momentary switch could be used to eliminate the need for a second switch. Multiple contact momentary's have multiple contact points. For example; in a two contact point momentary switch, the switch is depressed part way and makes contact with the first terminal. When the switch is further depressed it makes contact with the next set of terminals. These switches are common in cameras where the first contact activates the light intensity sensor and the second contact point takes the picture. In our case, if the aerosol canister is partially depressed downward, the visual display is re-energized displaying the current number of doses administered. If the canister is further depressed a dose of medication in released and the counter is incremented.

Another objective is to allow some way to reset the counter when the aerosol canister is replaced with a new aerosol canister. This could be a separate button or switch. A multiple contact momentary switch could also be used to reset the counter. For example; if the switch is partially depressed to the first contact point for a significant period of time it might reset the counter.

Another objective is to use additional VLSI circuits or an on-board computer to make it relatively easy to add additional functions.

A computer or microprocessor and a stored program could be utilized to monitor and retrieve a vast amount of patient data. This could include the date, time, and amount of medication consumed by the patient. The data could periodically be extracted from the device and examined by the physician. The data could be extracted by providing some type of I/O connection in the form of a data bus and controls. A small single jack outlet would lend itself to miniaturization. The device could also be used in conjunction with a modem to dump the data to a remote computer for analysis.

Another objective would be to provide a device that could keep track of the day and time a patient last took medication. This would allow a patient to check this data in the event that they do not remember when the last dose was administered. The information could be stored over several days allowing the patient or doctor to have a full profile of how medication was administered over time. This would require the display to be modified to display more than just a count, but date and time information as well.

Another objective is to provide counting devices for medication dispensers of different forms. The invention could also be easily adapted for use with less common cylindrical dispenser or other dispensers shapes.

DESCRIPTION OF THE PREFERRED EMBODIMENTS OF THE INVENTION

Figure 1A:
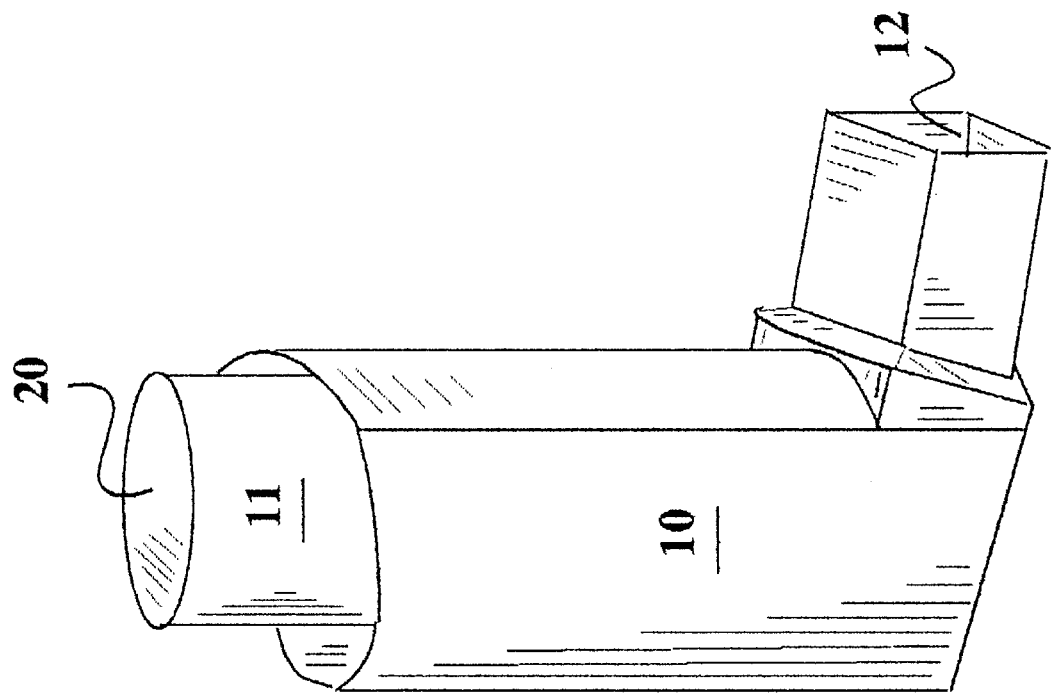
FIG. 1a is a side perspective view of a L-shaped metered doses delivery vehicle and aerosol canister.
Figure 1B:
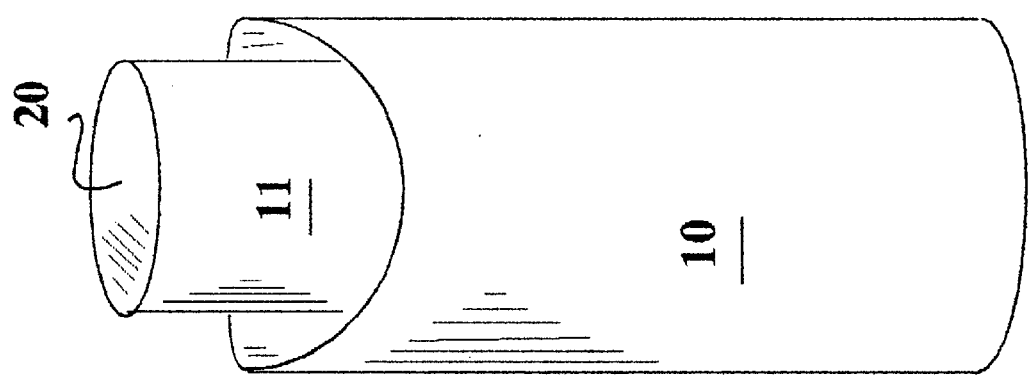
FIG. 1b is a rear perspective view of a L-shaped metered doses delivery vehicle and aerosol canister.
Figure 2:
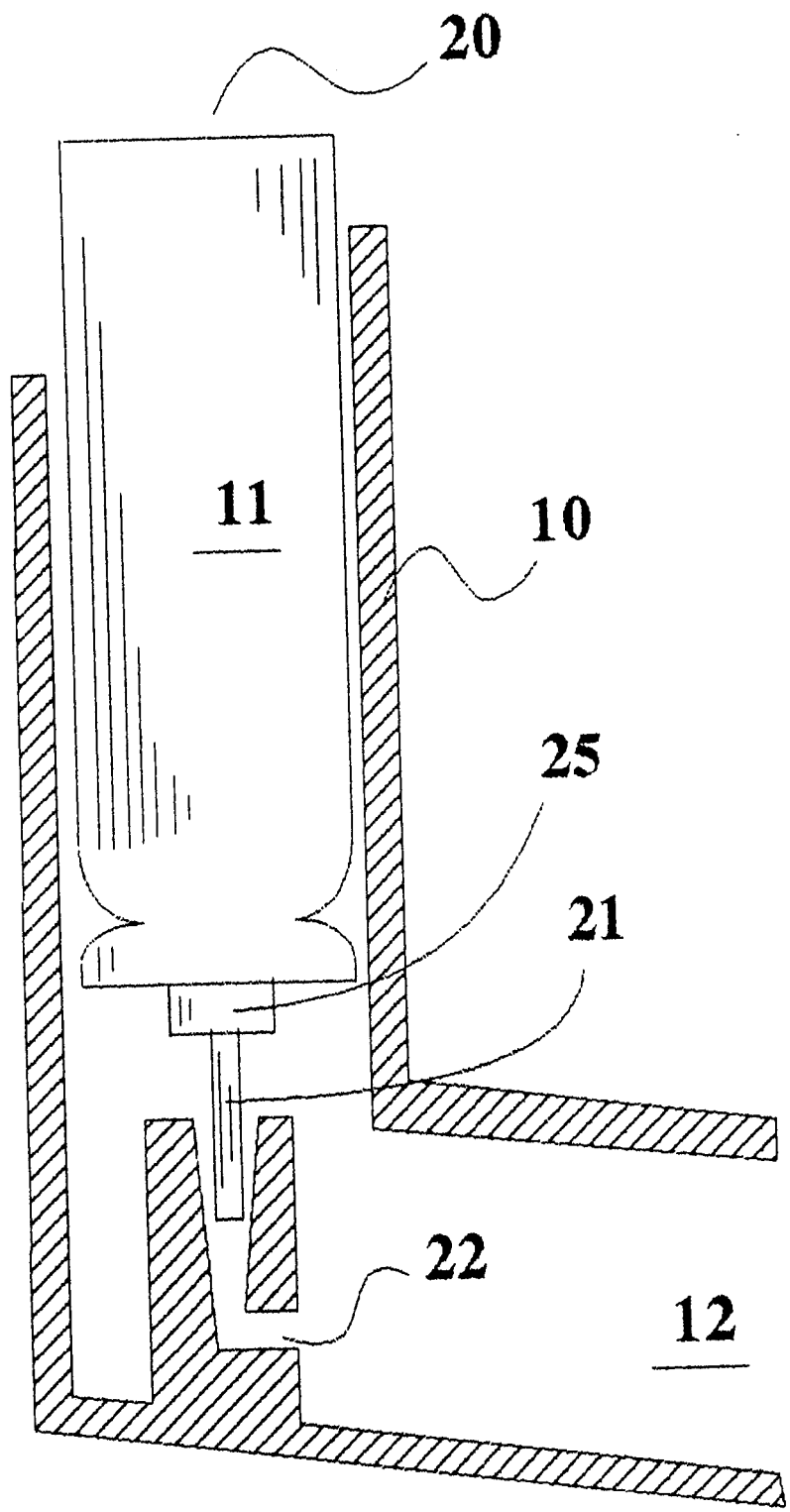
FIG. 2 is a side plan view of a L-shaped metered doses delivery vehicle and aerosol canister.
Figure 3:
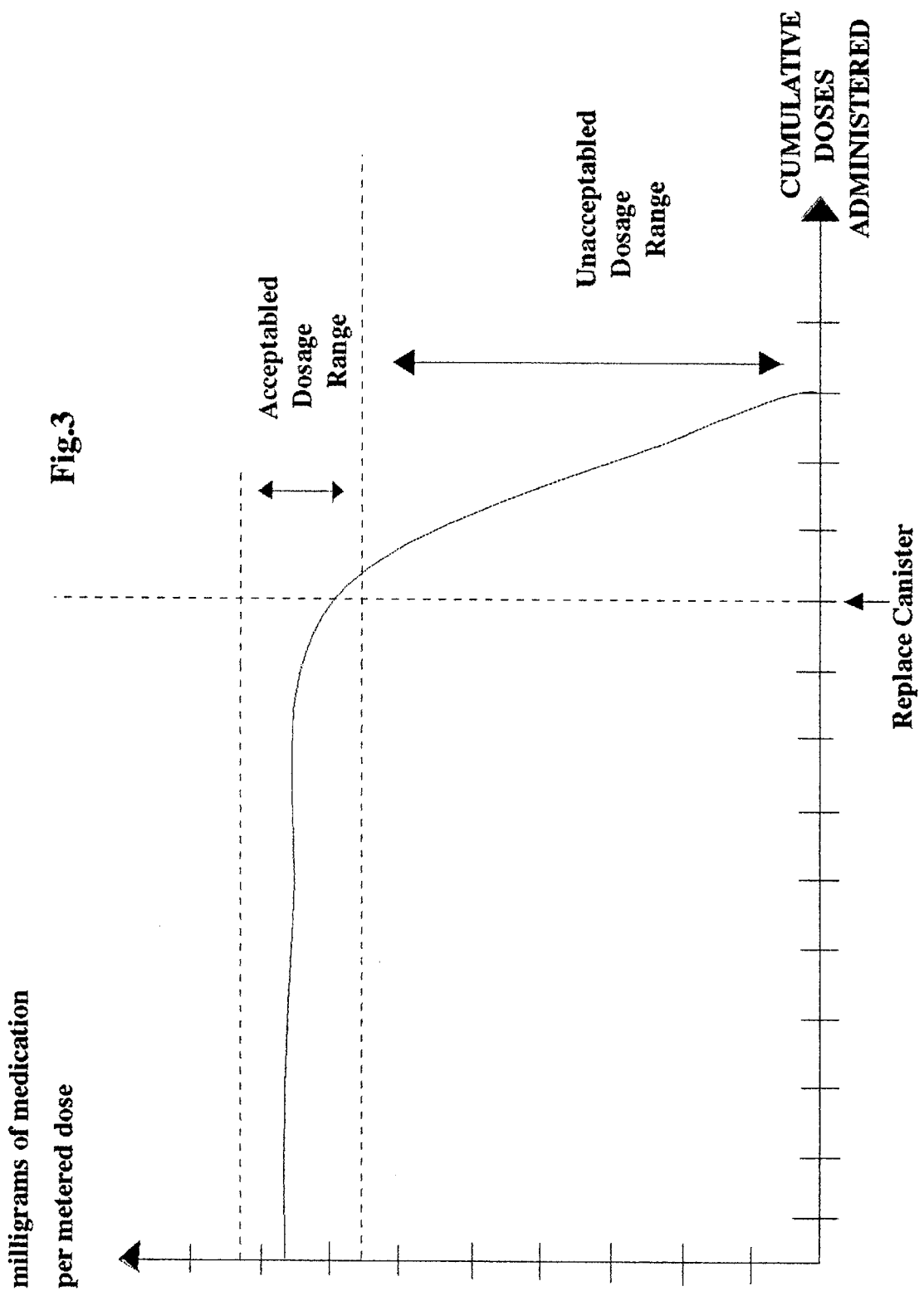
FIG. 3 is a graph of the milligrams of medication per metered dose versus cumulative doses administered for a typical aerosol canister.

FIGS. 1, 2, and 3 illustrate a common metered dose inhalation device widely used today by many patients. FIG. 1a is a side perspective view of a L-shaped metered dose delivery vehicle and aerosol canister. FIG. 1b is a rear perspective view of a L-shaped metered dose delivery vehicle and aerosol canister. FIG. 2 is a side plan view of a L-shaped metered dose delivery vehicle and aerosol canister. An examination of FIG. 1 and FIG. 2 help illustrate how a metered dose aerosol medication device is used. Aerosol canister 11 is inserted in L-shaped medication dispenser 10. The patient inhales the medication through opening 12 of the L-shaped metered dose inhalation device 10.

FIG. 2 illustrates how a downward pressure applied to 20, the top of the metered dose aerosol canister 11, forces the hollow stem 21 back into the aerosol canister 11. When the hollow stem 21 has moved sufficiently into canister 11 to open an internal valve, a meter dose of the aerosol medication is released under pressure through the hollow stem 21 and out through opening 22. The aerosol medication continues to travel out through opening 12 of the L-shaped medication dispenser 10 where it can be inhaled by the patient.

FIG. 3 is a graph that illustrates the operation of a typical aerosol canister. It is a plot of milligrams of medication per metered dose versus the cumulative number of doses expelled from the aerosol canister. There is a window of operation in which the amount of medication received from each dose may vary slightly but is well within the acceptable range. After some maximum number of doses the canister will still continue to expel medication, but the amount of medication will fall below an acceptable amount per dose.

FIGS. 4 through 9 illustrate the present preferred forms of the invention which includes a counter 40, which is attached to a modified L-shaped aerosol inhaler 10. A standard metered dose aerosol canister 11 can be used with the invention.

Figure 4A:
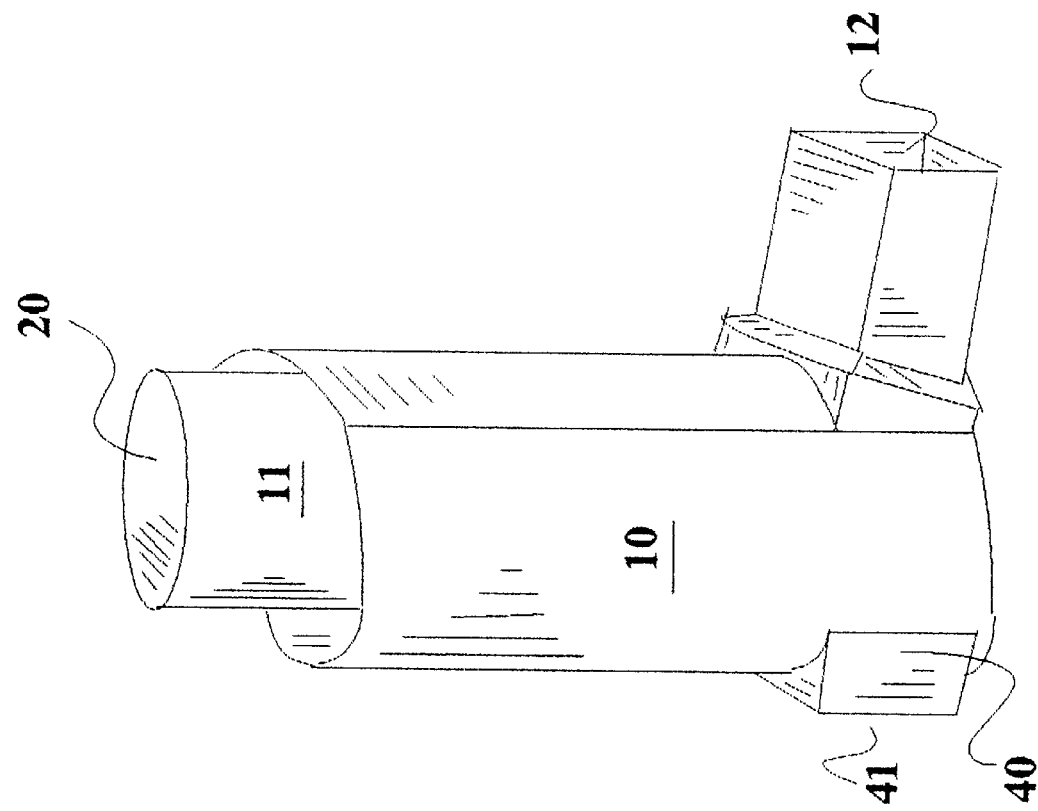
FIG. 4a is a side perspective view of a L-shaped metered doses delivery vehicle, aerosol canister, and counter.
Figure 4B:
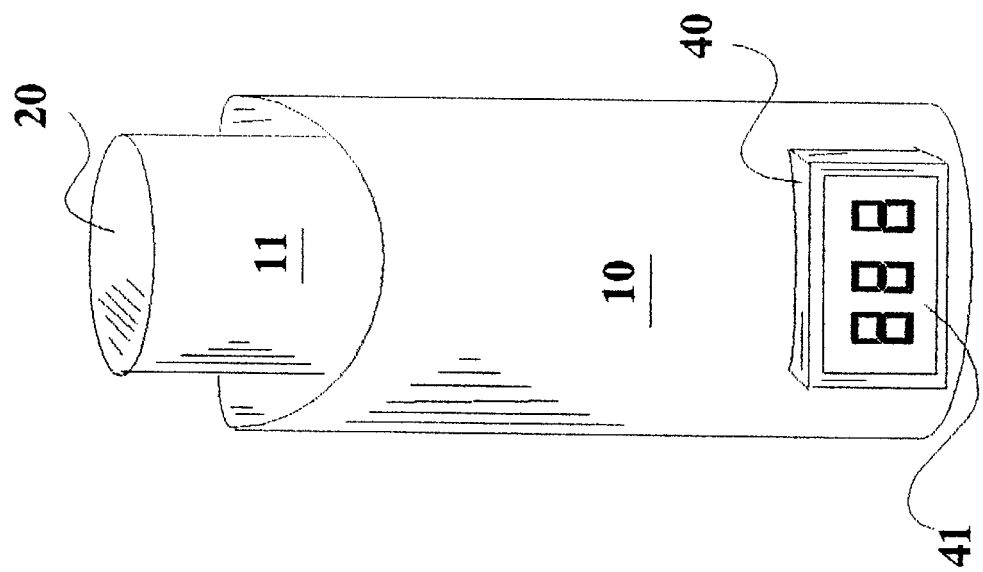
FIG. 4b is a rear perspective view of a L-shaped metered doses delivery vehicle, aerosol canister, and counter.
Figure 5:
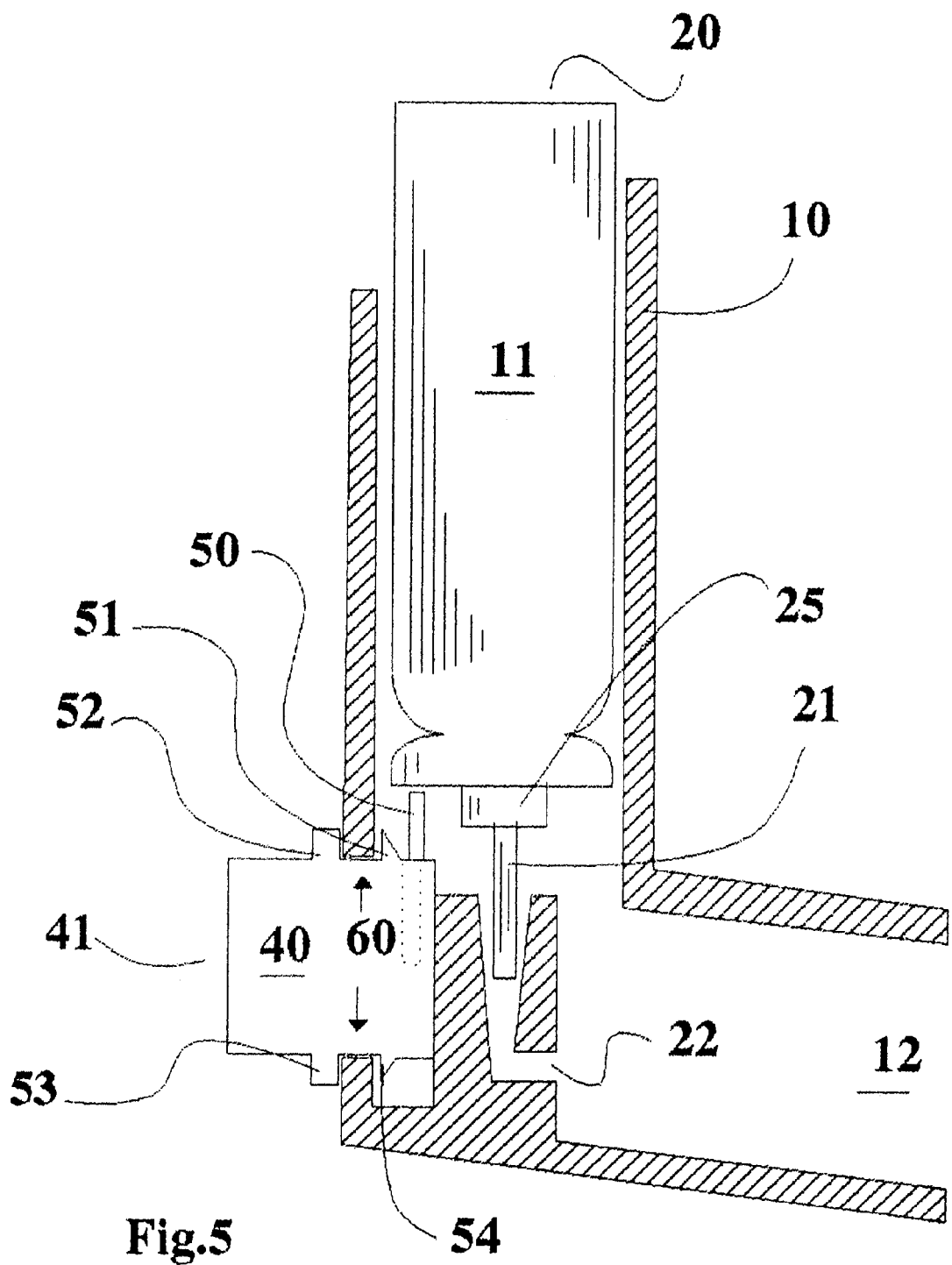
FIG. 5 is a side plan view of a L-shaped metered doses delivery vehicle, aerosol canister, and counter.
Figure 6:
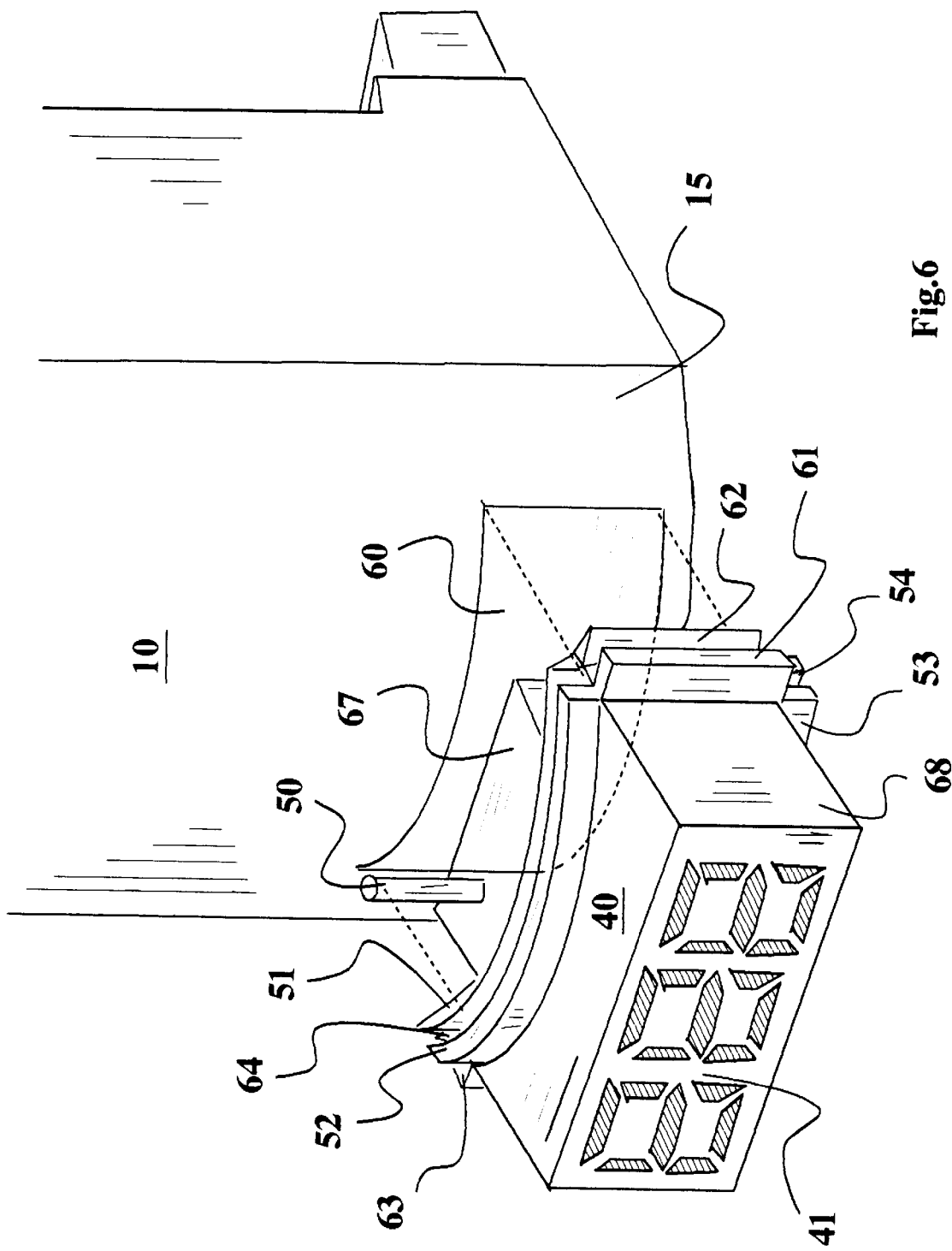
FIG. 6 is a rear-side exploded perspective view of a L-shaped metered doses delivery vehicle and counter.

FIGS. 4, 5, and 6 illustrate how counter 40 can be made useful by automatically counting the cumulative number of doses and how counter 40 can be attached to L-shaped metered dose delivery device 10.

FIG. 4a is a side perspective view of a L-shaped metered dose delivery vehicle 10, aerosol canister 11, and counter 40. FIG. 4b is a rear perspective view of a L-shaped metered dose delivery vehicle 10, aerosol canister 11, and counter 40.

The counter display face 41 is illustrated in FIG. 4b. The visible display 41 of counter 40 can also be seen in FIG. 4b.

FIG. 5 provides a side plan view of the counter 40 fastened to L-shaped metered dose delivery device 10. The counter 40 is fastened to L-shaped delivery device 10 by being inserted into opening 60 in L-shaped delivery device 10. Push button 50 is depressed into counter 40 and thus increments the count. The exterior of the counter is comprised of a material that has an elasticity property that allows top triangular protrusion 51 and bottom triangular protrusion 54 to deform, allowing the rear portion of counter 10 to be inserted through opening 60 of L-shaped dispenser 10. Once triangular protrusions 51 and 54 pass through opening 60 they return to approximately their original shape as illustrated in FIG. 5. Inside top protrusion 51, outside top protrusion 52, inside bottom protrusion 54, and outside bottom protrusion 53 allow the counter to be securely fastened to L-shaped delivery device 10. Protrusions 51, 52, 53, and 54 each have a portion of their surface that is substantially parallel to portions of surfaces of L-shaped container 10, in which they are substantially in contact. Said substantially parallel contacting surfaces of protrusions 51, 52, 53, and 54 are roughly perpendicular to the surfaces of counter 40 from which they protrude. This configuration protrusions 51, 52, 53, and 54 is the means by which counter 40 is attached to L-shaped delivery device 10.

There are many materials that have an acceptable elasticity property to achieve the protrusion characteristics just described. These include some metals, some hard rubbers and many plastics; such as high density polyethylene.

FIG. 5 also illustrates how a downward pressure applied to 20; the top of the metered dose aerosol canister 11, forces the hollow stem 21 back into the aerosol canister 11, and at the same time forces push button momentary switch 50 to contact and increment counter 40, by being depressed and pushed into counter 40. When hollow stem 21 has moved sufficiently into canister 11, to open an internal valve, a meter dose of the aerosol medication is released under pressure through the hollow stem 21 and out through opening 22. The aerosol medication continues to travel out through opening 12 of the L-shaped dispenser 10, where is can be inhaled by the patient. Visual display 41 displays the current count.

FIG. 6 is a rear-side exploded perspective view of counter 40, positioned to be inserted into L-shaped metered dose delivery device 10. Counter 40 becomes fastened to L-shaped delivery device 10 by being inserted into opening 60, in L-shaped delivery device 10. The counter 40 is incremented when push button 50 is depressed into counter 40. This occurs when aerosol canister 11 is depressed to release medication. Again, the exterior of the counter is comprised of a material that has an elasticity property that allows top triangular protrusion 51 and bottom triangular protrusion 54 to deform, allowing the rear portion of counter 10 to be inserted through opening 60 of L-shaped dispenser 10. Once triangular protrusions 51 and 54 pass through opening 60 they return to approximately their original shape as illustrated in FIG. 5. Inside top protrusion 51, outside top protrusion 52, inside bottom protrusion 54, and outside top protrusion 53 are used to securely fasten counter 40 to L-shaped delivery device 10. Protrusions 51, 52, 53, and 54 each have a surface that is substantially parallel to the portions of the surfaces of L-shaped inhaler 10, in which they are substantially in contact. Top protrusions 51 and 52 and bottom protrusions 53 and 54 are slightly curved, to match the horizontal curve of rear wall 15 of the L-shaped delivery vehicle 10.

FIG. 6 also illustrates right side protrusions 61 and 62 and left side protrusions 63 and 64 which further help attach the counter to L-shaped inhaler device 10. Protrusions 62 and 64 are roughly triangular and protrusions 61 and 63 are roughly rectangular. Protrusions 61, 62, 63, and 64 are not curved but are straight to match the vertical shape of rear wall 15 of L-shaped delivery vehicle 10.

In FIG. 6 triangular protrusions 51, 54, 62, and 64 extend the full length of the side of the counter from which they protrude. Small tabs that extend along only a small portion of the counter sides from which they attach, would also prove effective at securing counter 40 to L-shaped delivery device 10.

Rear half 67 of counter 40 is shown to be slightly smaller than the front half 68 of counter 40 in FIG. 6. The rear half 67 can also be constructed to be about the same size as the front half 68 of counter 40. The sizes are shown to be different in FIG. 6 simply to illustrate that this is a design choice. If it is desired to have a slightly larger display or to add additional functions or features, the additional components can be accommodated by making the front half 68 of counter 40 larger.

Figure 7:
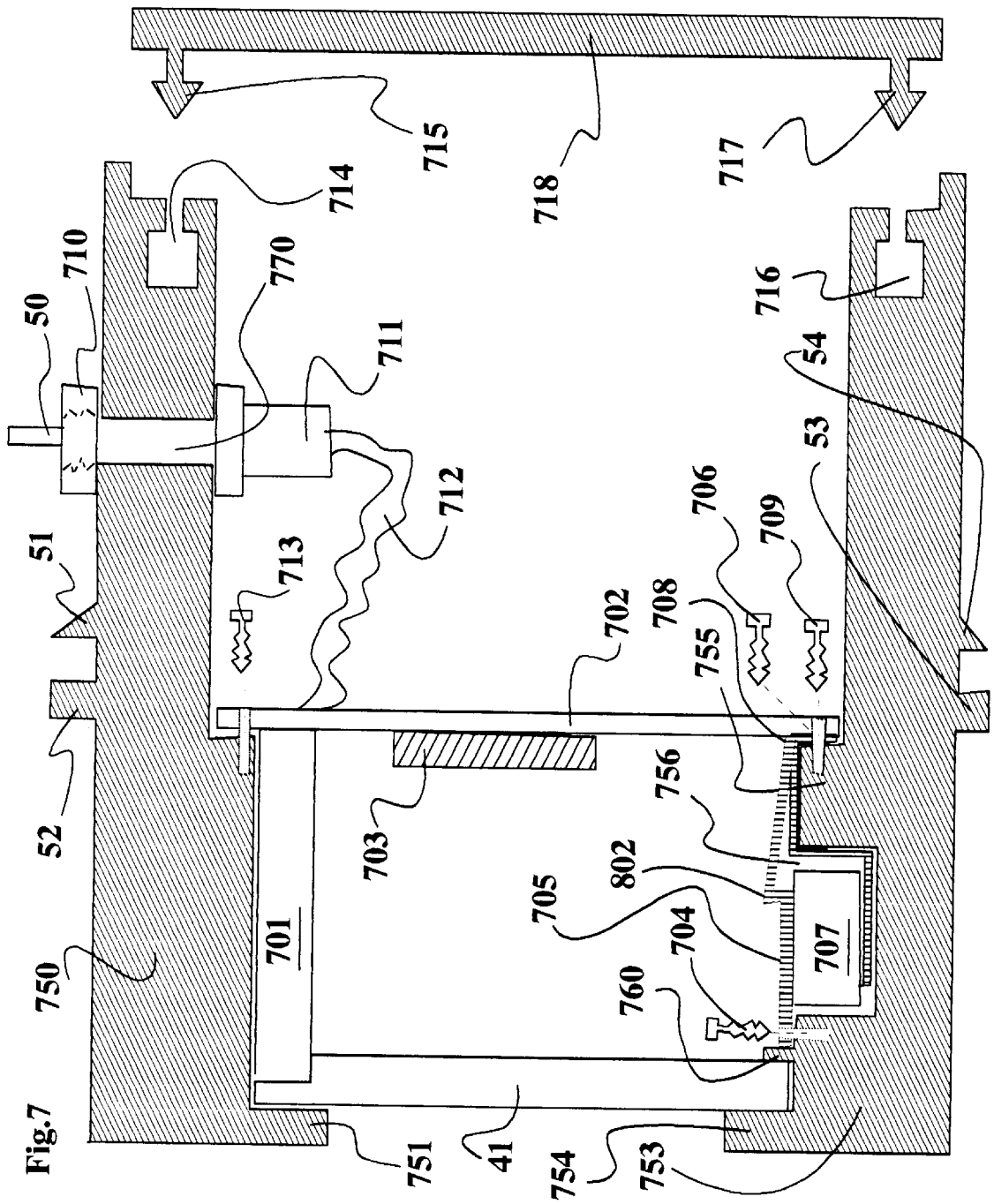
FIG. 7 is a side plan view of the counter.

FIG. 7 illustrates a side plan view of counter 40. Visual display 41 is held in place at the front of counter 40 by being placed against top wall protrusion 751 of top counter wall 750 and bottom wall protrusion 754 of bottom counter wall 753. Semi-rigid member 701 has a dual purpose; it holds the top portion of the display against top protrusion 751, and it also contains wires which allow the display driving signals to propagate from VLSI logic chip 703, through circuit board 702 to display 41. The combination of circuit board 702 and screw 713 exert a force on member 701, which in turn holds the top portion of display 41 substantially against top protrusion 751. The bottom of display 41 is first inserted between bottom protrusions 754 and 760, of bottom counter wall 753, during the manufacturing process and hold the bottom of display 41 substantially in place.

Figure 8:
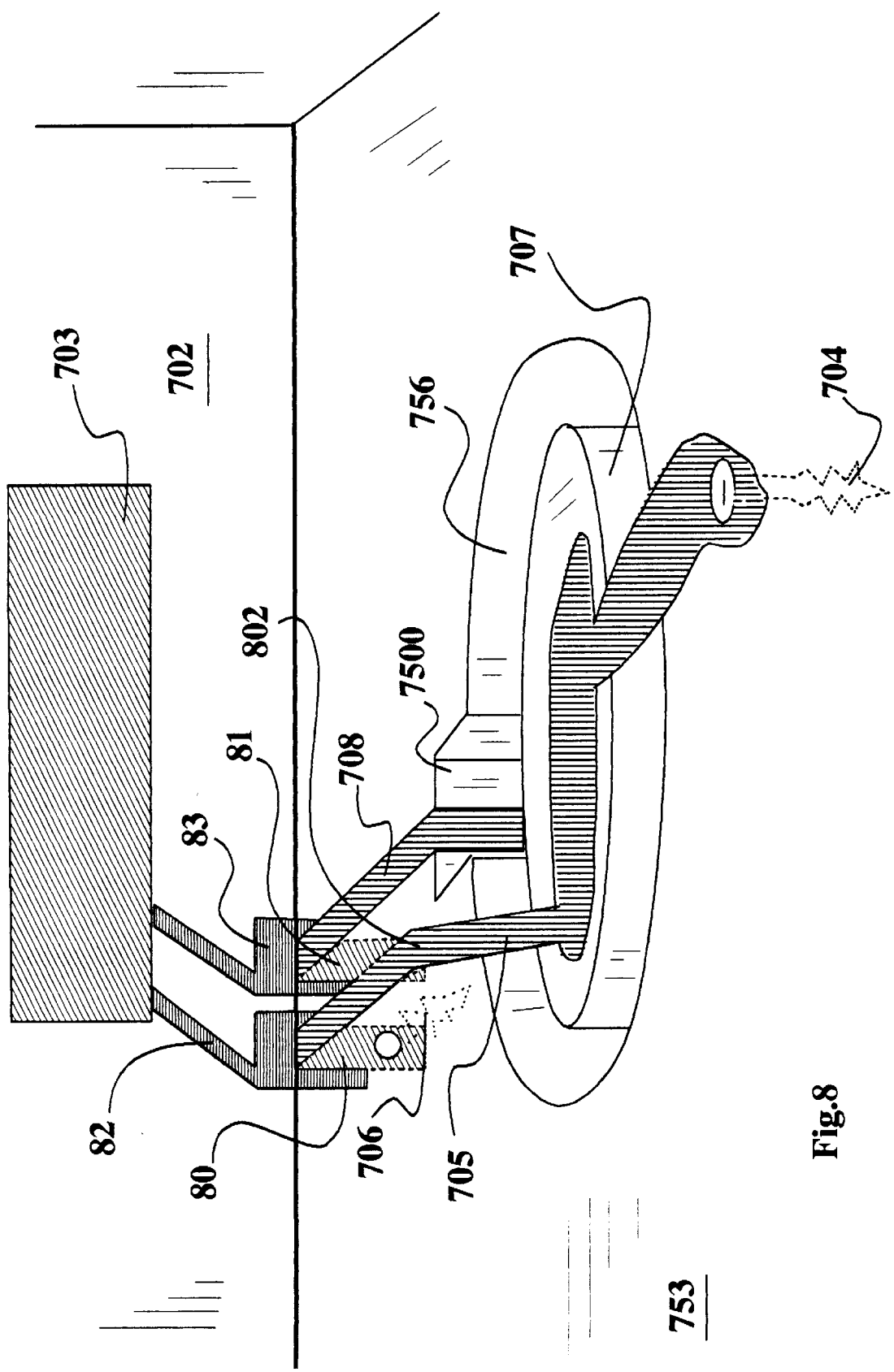
FIG. 8 is a front-side perspective view of the battery, connectors, and circuit board, and integrated circuit layout.

FIG. 7 and FIG. 8 illustrate how battery 707 is held substantially in place and delivers power to the circuits on VLSI chip 703 via circuit board 702. Cylindrical battery 707 is inserted into the cylindrical opening 756 in bottom wall 753. The bottom of the battery 707, which is normally the negative pole of battery 707, feeds power to circuit board 702 via conductor 708. Conductor 705 has kink 802 which helps secure it in place on the top of battery 707. Conductors 705 and 708 are made of a suitable metal. Conductor 705 is slightly deformed when held in place by screw 704 and 706. This slight deformation is due to kink 802 and creates a force that holds conductor 705 substantially against battery 707.

FIG. 8 illustrates niche hole 7500, made in cylindrical opening 756, of bottom wall 753, prevent conductor 708 from contacting the side wall of battery 707.

FIG. 7 and FIG. 8 also illustrates that the top of battery 707, which is normally the positive pole of battery 707, is connected to circuit board 702, via conductor 705. Conductor 705 is held in between circuit board 702 and protrusion 755 by screw 706 which produces a forward force against circuit board 702. Conductor 705 is also used to hold battery 707 substantially in place.

FIG. 7 also illustrates integrated circuit 703 attached to circuit board 702. The circuitry contained on this integrated circuit will be described in some detail later in this disclosure.

FIG. 7 illustrates momentary contact switch 711 which is connected electrically to circuit board 702 via wire pair 712. Components are normally mounted on a single side of a circuit board to simplify the manufacturing process. Wire connections are normally made to the same side for the same reason. However, there are situations where due to the need to make a device that is very compact, components are mounted on both sides of the circuit board. Construction using either method is possible for this device. There are many well known methods in the art that allow momentary contact switch 711 to be mounted to wall 750 of counter 40. In FIG. 7 momentary contact switch 711 is attached to top wall 750, by being inserted through opening 770. Nut 710 is used to secure 750 by being screwed to the threaded top of momentary switch 711. The bottom base of momentary switch 711 is larger than opening 770 in upper wall 750. The combined force of the base pressing upward against wall 750 and nut 710 pushing down, hold momentary switch 711 substantially in place. Momentary switch 711 could also be mounted on circuit board 702, which could possibly reduce the manufacturing cost of the device. In this case the circuit board would be moved further back in the device, so that the momentary switch can be properly aligned with the movement of the aerosol canister. It is also possible to move the battery to the side of 753 behind circuit board 702. This would allow the battery to be more easily replaced.

Figure 9:
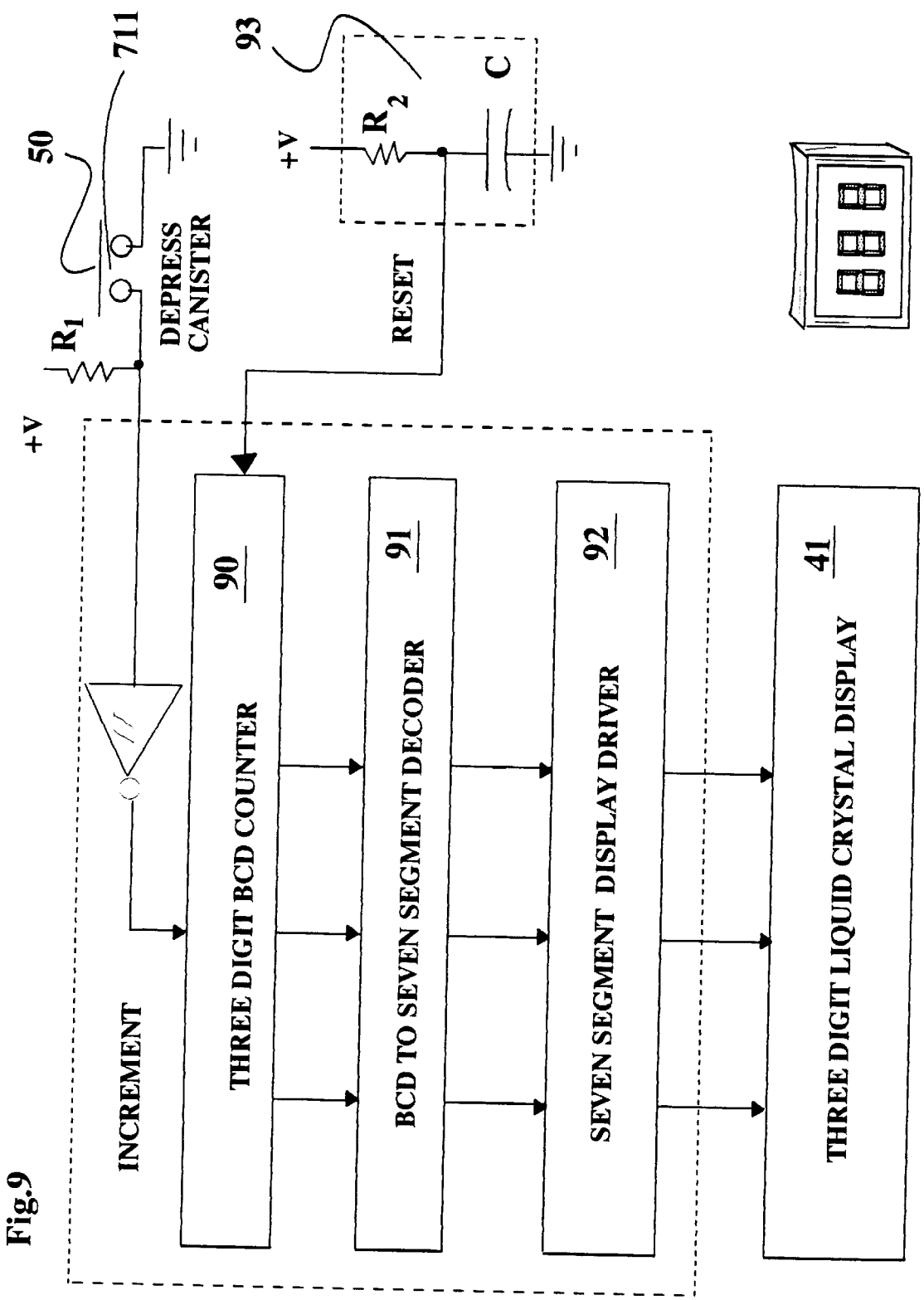
FIG. 9 is a diagram of the counter circuit.

FIG. 7 shows only a single momentary switch 711 used to increment the counter. FIG. 9 illustrates that BCD (Binary Coded Decimal) counter circuit 90 is reset when battery 707 is inserted into counter 40 and thus applying voltage +V to RC circuit 93. This produces a slightly delayed reset pulse that resets BCD counter circuit 90. There could also be an additional counter employed, so that if the push button 50 of momentary switch 711 is depressed for a significant period of time, the counter is reset. This would allow the patient to depress aerosol canister 11 that has expended all it's metered doses and reset the counter 40. The old aerosol canister could be removed and a new aerosol canister could then be inserted with visual display 41 of counter 40 displaying zero.

FIG. 7 illustrates how back counter wall 718 attaches to the counter by the insertion of triangular tab member 715, into top counter wall opening 714 and by inserting triangular tab member 717 into bottom wall opening 716.

FIG. 8 illustrates how conductor 705 has a section 80 that is positioned between protrusion 755 of counter wall 753 and circuit board 702. Conductor section 80 is held against circuit board conductor 82 by screw 706, which allows power to be routed from battery 707 positive pole to logic chip 703. FIG. 8 also illustrates how conductor 708 has a section 81 that is routed between protrusion 755 of counter wall 753 and circuit board 702. Conductor section 81 is held against circuit board conductor 83 by screw 709, which allows power to be routed from battery 707 negative pole to logic chip 703.

FIG. 9 illustrates the most basic logic circuits needed to produce a counter that automatically increments when the aerosol canister is depressed to release medication. Push button 50 of momentary switch 711 is depressed when the aerosol canister 11 is depressed to release a dose of medication. Momentary switch 711 thus grounds the connection to which R1 has held a +V which in turn forces the output of the Schmitt trigger inventer circuit 95 to a logical "1" state. The BCD (Binary Code Decimal) counter 90 is incremented on the edge of the transition from "0" to "1". A circuit with a hysteresis operation like a Schmitt trigger inventer, can be used to prevent any false counter increment pulse due to possible bouncing of the momentary switch.

FIG. 9 also illustrates how three digit BCD counter 90 feeds into a BCD to seven segment decoder 91, which generates the proper patterns for the segments of the LCD (Liquid Crystal Display) 41. BCD to seven segment decoder 91 then feeds through display driver circuits that generate the signals needed to drive the LCD display. All of these circuits are common place in the art.

Figure 10:
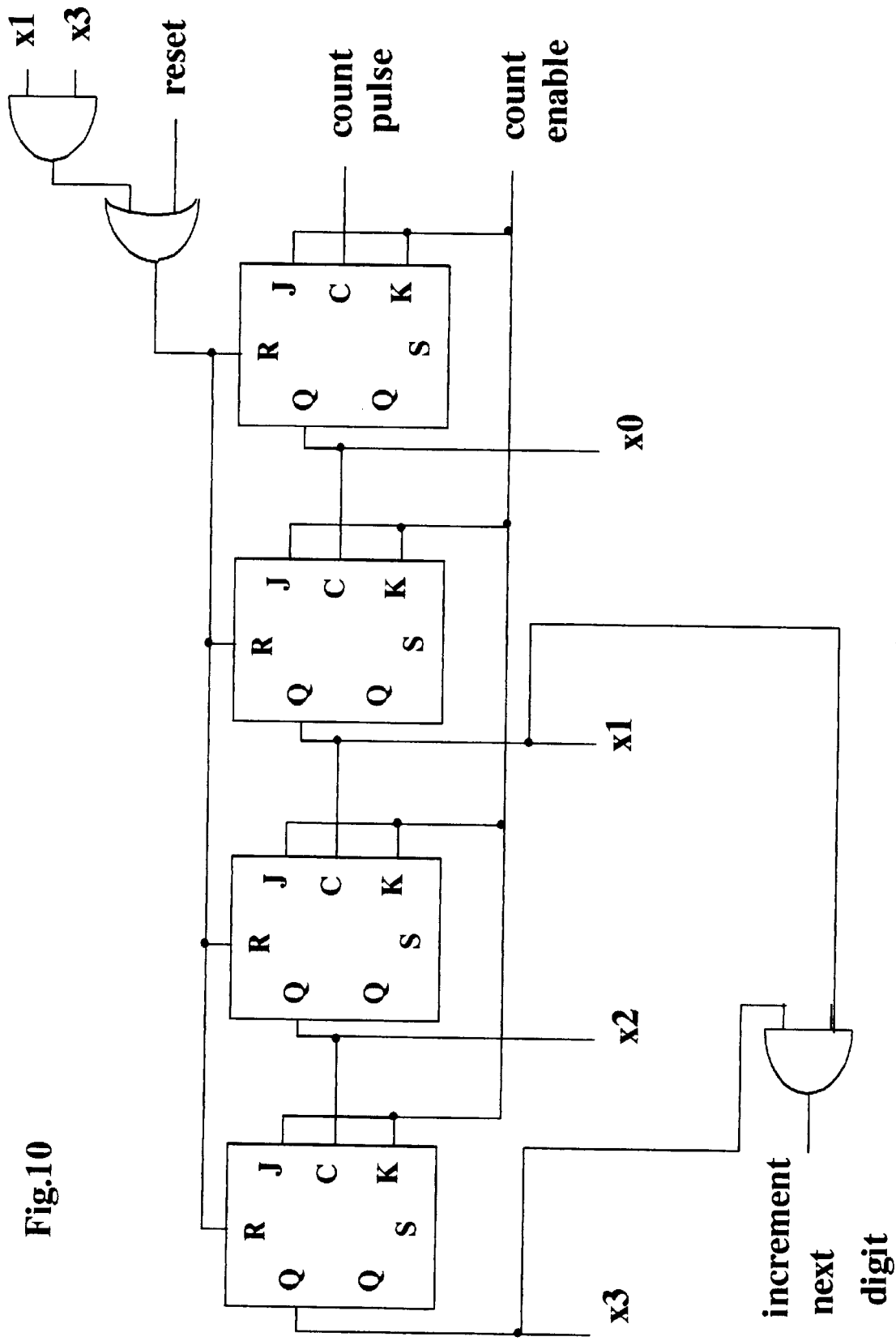
FIG. 10 is a detailed logic diagram of the BCD counter circuit.

FIG. 10 illustrates a BCD counter comprised of four clock JK flip flops with set and reset signals. The signals x0, x1, x2, and x3 represent the least significant to most significant bits of the binary coded decimals. On a positive transition of a JK flip flop the output of the latch Q will switch states when both J and K inputs are at a logical "1". This corresponds to the "count enable" signal in FIG. 10. If the J and K inputs are both at a logical "0" the latch will not change state on a positive clock transition. The R "reset" line will always change the latch output "Q" to a logical "1" state independent of the state of the clock. In the circuit in FIG. 10 the AND of x1 and x3 which correspond to the value "10" in decimal coincide with the reset of the latches to "0". In other words the circuit will count from 0 sequentially to 9 and then go back to 0. The AND of x1 nd x1 are also used to provide an "increment next digit" signal to the next counter stage. There is a separate reset signal that can also rest the latches to 0. Again the signals from the BCD counter are fed to a decoder stage to then directly to the display.

I am claiming no invention in the circuit, so I end my description of the operation of the device with only this brief description of the BCD (Binary Coded Decimal) counter of FIG. 10. I end here without going into the specifics of the latches and logic gate or the specific transistor configuration of the logic circuits. I will again mention, however that circuit 93 is configured with a resistor R2 and a capacitor C in such a way as to generate a delayed reset pulse, when the battery is inserted into the circuit.

The invention in its broader aspect is not limited to the specific described embodiments and departures may be made therefrom within the scope of the accompanying claims without departing from the principals of the invention and without sacrificing its chief advantages.

What I claim is:

1. An inhalation device, comprising:

a housing;

a container of medicine received in the housing;

a delivery system for dispensing a predetermined dose of medicine from the container for inhalation by a user;

a counter attached to the housing;

a display coupled to the counter; and a switch actuated by the container of medicine, for controlling operation of the counter and display of data on the display, the switch including first and second actuating positions;

wherein, in the first actuating switch position, a cumulative number of doses of the medicine dispensed from the container is counted by the counter and displayed on the display; and wherein, in the second actuating switch position, the counter is incremented if the second actuating switch position is maintained for less than a predetermined period of time, and counter is reset to zero if the second actuating switch position is maintained for greater than the predetermined period of time.

2. The inhalation device according to claim 1, wherein the housing includes an opening, and wherein the inhalation device further included a system for securing the counter within the opening.

3. An inhalation device, comprising:

a housing;

a container of medicine received in the housing;

a delivery system for dispensing a predetermined dose of medicine from the container for inhalation by a user;

a counter attached to the housing;

a display coupled to the counter; and a switch actuated by the container of medicine, for controlling operation of the counter and display of data on the display, the switch including first and second actuating positions;

wherein, in the first actuating switch position, a cumulative number of doses of the medicine dispensed from the container is counted by the counter and displayed on the display; and wherein, in the second actuating switch position, the counter is incremented if the second actuating switch position is maintained for less than a predetermined period of time, and counter is reset to zero if the second actuating switch position is maintained for greater than the predetermined period of time;

wherein, the housing includes an opening, and wherein the inhalation device further included a system for securing the counter within the opening;

wherein, the system for securing the counter with the opening includes a first set of protrusions configured to be inserted into the interior of the housing through the opening and to engage a inner surface of the housing adjacent the housing, and a second set of protrusions for engaging an outer surface of the housing adjacent the opening, the first and second set of protrusions coacting to securely fasten the counter to the housing.

4. The inhalation device according to claim 3, wherein the first set of protrusions have a triangular configuration to facilitate insertion of the first set of protrusions through the opening.

5. The inhalation device according to claim 3, wherein the first and second sets of protrusions are shaped to conform to a peripheral shape of the housing adjacent the opening.

6. An inhalation device, comprising:

a housing;

a container of medicine received in the housing;

a delivery system for dispensing a predetermined dose of medicine from the container for inhalation by a user;

a modular component including a counter coupled to a display;

a system for securing the modular component to the housing, including an opening; and a switch, positioned within the housing, actuated by the container of medicine, for controlling operation of the counter and display of data on the display, the switch including first and second actuating positions;

wherein, in the first actuating switch position, a cumulative number of doses of the medicine dispensed from the container is counted by the counter and displayed on the display;

wherein, the system for securing the counter with the opening includes a first set of protrusions configured to be inserted into the interior of the housing through the opening and to engage a inner surface of the housing adjacent the housing, and a second set of protrusions for engaging an outer surface of the housing adjacent the opening, the first and second set of protrusions coacting to securely fasten the counter to the housing.

7. The inhalation device according to claim 6, wherein the first set of protrusions have a triangular configuration to facilitate insertion of the first set of protrusions through the opening.

8. The inhalation device according to claim 6, wherein the first and second sets of protrusions are shaped to conform to a peripheral shape of the housing adjacent the opening.

9. The inhalation device according to claim 6, wherein, in the second actuating switch position, the counter is incremented if the second actuating switch position is maintained for less than a predetermined period of time, and counter is reset to zero if the second actuating switch position is maintained for greater than the predetermined period of time.

* * * * *